(12) United States Patent
Grodum

(10) Patent No.: US 8,478,622 B2
(45) Date of Patent: Jul. 2, 2013

(54) SYSTEM AND METHOD FOR SCHEDULING CONFERENCE RESOURCES

(75) Inventor: Nicolai Grodum, Oslo (NO)

(73) Assignee: Cisco Technology, Inc., San Jose, CA (US)

( * ) Notice: Subject to any disclaimer, the term of this patent is extended or adjusted under 35 U.S.C. 154(b) by 1399 days.

(21) Appl. No.: 11/721,740

(22) PCT Filed: Dec. 13, 2005

(86) PCT No.: PCT/NO2005/000460
§ 371 (c)(1),
(2), (4) Date: May 28, 2008

(87) PCT Pub. No.: WO2006/065148
PCT Pub. Date: Jun. 22, 2006

(65) Prior Publication Data
US 2009/0112671 A1    Apr. 30, 2009

(30) Foreign Application Priority Data
Dec. 14, 2004    (NO) .................................. 20045443

(51) Int. Cl.
*G06Q 10/00* (2012.01)
(52) U.S. Cl.
USPC ........................................................ 705/7.12
(58) Field of Classification Search
USPC .................................................. 705/8, 7.12
See application file for complete search history.

(56) References Cited

U.S. PATENT DOCUMENTS

| | | | |
|---|---|---|---|
| 7,693,734 B2* | 4/2010 | Christenson et al. ........ 705/7.19 |
| 2002/0131572 A1 | 9/2002 | Paradis |
| 2002/0184063 A1* | 12/2002 | Kaufman et al. ................. 705/7 |
| 2002/0188490 A1 | 12/2002 | Kruse |
| 2003/0005055 A1* | 1/2003 | Ralston et al. ................. 709/204 |
| 2004/0064355 A1* | 4/2004 | Dorenbosch et al. ............. 705/9 |
| 2004/0093290 A1* | 5/2004 | Doss et al. ........................ 705/35 |
| 2004/0216123 A1* | 10/2004 | Seebaldt ........................ 719/310 |
| 2005/0027581 A1* | 2/2005 | Kjesbu et al. ..................... 705/8 |
| 2005/0034079 A1* | 2/2005 | Gunasekar et al. ............ 715/753 |
| 2006/0062367 A1* | 3/2006 | Christenson et al. ..... 379/202.01 |
| 2009/0112671 A1* | 4/2009 | Grodum ........................... 705/8 |

FOREIGN PATENT DOCUMENTS
WO    2004 077237    9/2004

OTHER PUBLICATIONS

Video Communiations Management Software: Critical Success Factors for Technology Decision Makers 2005: LifeSize Communications, Inc.*

* cited by examiner

*Primary Examiner* — Andre Boyce
*Assistant Examiner* — Ernest A Jackson
(74) *Attorney, Agent, or Firm* — Oblon, Spivak, McClelland, Maier & Neustadt, L.L.P.

(57) ABSTRACT

The present invention relates to managing and scheduling videoconferences. It introduces a novel mechanism for scheduling a virtual resource connected to an individual or a group of individuals. The virtual resource is associated to one or more conference systems in a conference management system, and an entity representing the virtual re-source is displayed in a conventional resource planning application (e.g. Microsoft Outlook) allowing a user to investigate if the virtual resource, i.e. at least one of the conference systems, is free or busy. The user is then able to schedule a conference with the resource by a familiar scheduling interface, and without having to know with which alternative conference systems the individual or group of individuals connected to the virtual resource is associated.

8 Claims, 3 Drawing Sheets

SYSTEM AND METHOD FOR SCHEDULING CONFERENCE RESOURCES

FIELD OF THE INVENTION

The present invention relates to managing and scheduling videoconferences.

BACKGROUND OF THE INVENTION

Conventional videoconferencing systems comprise a number of end-points communicating real-time video, audio and/or data streams over and between various networks such as WAN, LAN and circuit switched networks.

A number of videoconference systems residing at different sites may participate in the same conference, most often, through one or more MCU's (Multipoint Control Unit) performing i.a. switching functions to allow the audiovisual terminals to intercommunicate properly.

As videoconferencing involves various recourses and equipment simultaneously interoperating at different localizations and capabilities, there is a need for the possibility to manage the resources involved both for scheduled and ad hoc videoconferences. The wording schedule or scheduler shall also be understood as including setting up ad-hoc meetings or calls.

Videoconferencing systems are therefore often used in conjunction with a resource scheduler. A resource scheduler is a module that is used to schedule or book resources at any given point in time. The resource scheduler will allow a user to request resource usage at a given time, and either allow or disallow the usage at that time. Resource schedulers are often used for scheduling the use of meeting rooms, network resources, video systems etc. The resource scheduler must be connected to a database containing updated information regarding all accessible resources like MCU's, gateways, routers, end-points etc.

A resource scheduler may e.g. provide system and resource overview, allowing the user to create, edit, and delete reservations, reserve resources for dial-in participants and specify bandwidth and network settings. The resource scheduler may also support automatic call routing and automatic selection of point-to-point connection, including one or more MCU's. The resource scheduler normally operates with an intuitive web interface requiring no additional installation on the user terminal other than a conventional web browser.

Even if users have audio or videoconferencing equipment available, either as personal or group systems, a great problem with scheduling meetings using audio- and videoconferencing equipment is knowledge of which resources are available to a given participant. In many cases, it is necessary for the one that is booking the conference to ask the participants in person about which localizations and systems etc. are accessible to them at the particular moment, and which accessories and services they have available or which is preferable. This manual "round-robin" request is added to the use of a resource scheduler, causing delay in conference booking and reducing the utilitarian value of the resource scheduler. The lack of knowledge regarding the participants' access and preferences is also the main reason that ad-hoc conferences are difficult to set-up—they simply require too much fluctuating knowledge of the far end side from the users.

Another problem regarding ad-hoc scheduling is that even if the resource scheduler knows that a certain end-point is available and ready for use, it cannot know whether the participants are present at the different sites, when the videoconference is not pre-scheduled. Ad-hoc booking will then normally also require manual requests in the form of additional calls to the participants in advance, making it behave like a pre-scheduled call.

SUMMARY OF THE INVENTION

It is an object of the present invention to provide a system and a method avoiding the above described problems.

The features defined in the independent claims enclosed characterise this system and method.

In particular, the present invention discloses a system adapted to schedule and/or investigate possibilities for a conference between two or more individuals for automatically reserving required conference systems wherein each individual or group of individuals are associated with one or more preferred conference systems in a conference management system keeping track of reservation status of the conference systems, including a resource planning application server adapted to create and maintain a virtual resource for each individual or group of individuals reflecting time-dependent possibility of conference participation of the respective individual or group of individuals according to reservation status of the conference systems associated with the respective individual or group of individuals, and a resource planning application including a user interface displaying the virtual resource allowing users to schedule a conference with the individual or groups of individuals in a time interval by the virtual resource implying a request to said resource planning application server to reserve for said time interval a free one of said virtual resource associated conference systems in the conference management system.

The present invention also discloses corresponding methods.

BRIEF DESCRIPTION OF THE DRAWINGS

In order to make the invention more readily understandable, the discussion that follows will refer to the accompanying drawings.

BEST MODE OF CARRYING OUT THE INVENTION

In the following, the present invention will be discussed by describing a preferred embodiment, and by referring to the accompanying drawings. However, people skilled in the art will realize other applications and modifications within the scope of the invention as defined in the enclosed independent claims.

The present invention introduces a novel mechanism for scheduling a virtual resource representing the conference system associated with a person/group presently being free. This resource is managed by a conference management system. The basic idea is to present this resource as one bookable entity associated with the user, even if the user has more than one conference system connected to him. When scheduling a conference, the one who carries out the scheduling does not need any information regarding the participants' preferred conferencing systems. Instead, the conference management system attempts to find the best possible video conference resources for the call, based on the users' pre-registered preferred conference systems, which also may be arranged in a prioritized order. Scheduling a conference will be as easy and intuitive as scheduling a regular meeting between Microsoft Exchange account holders through a Microsoft Outlook calendar. The present invention is well suited for integration with Exchange and Outlook, but it may also be utilised in any centralised scheduling or calendar programme, as e.g. Lotus. However, the present invention will be described in detailed by way of an example using Microsoft Exchange and Outlook.

Figure 1:
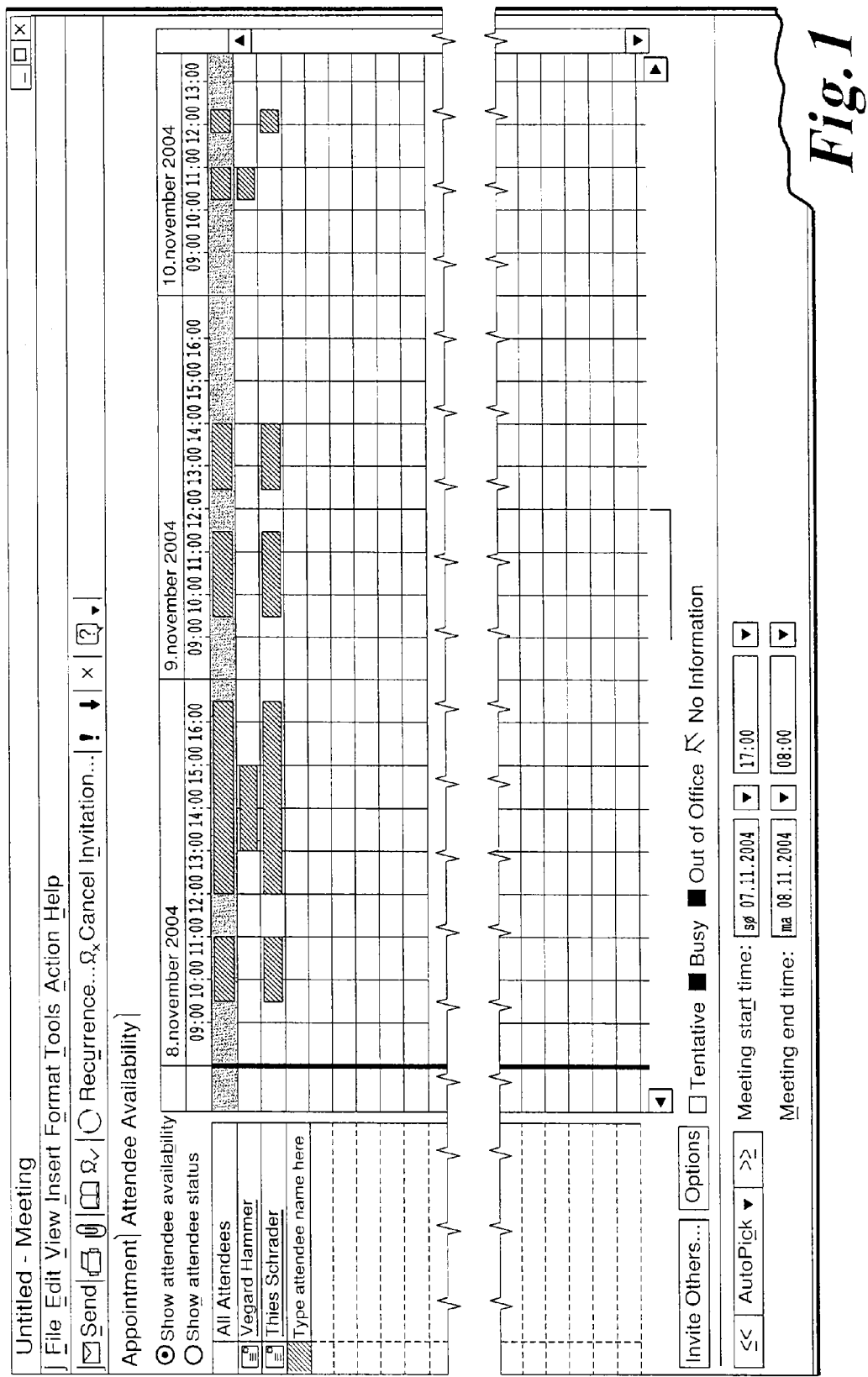
FIG. 1 shows an example of entries in the Attendee Availability interface of Microsoft Outlook.

When Microsoft Outlook is working towards Exchange, a user account for each user is created. FIG. 1 illustrates how such user accounts may appear in a conventional Outlook scheduling session. The schedule of each potential meeting participant is displayed as a time bar lined up with the respective participant names. The periods in which the participants are busy are marked blue. A common bar is shown on top, displaying the combined schedule of all the potential participants. The person scheduling the meeting can then easily select a meeting time suitable for all the participants, and distribute an invitation.

The present invention introduces additional accounts, referred to as virtual resource accounts. These virtual resource accounts are associated with respective individuals (or a group of individuals) and correspond to one or more conference systems registered in a conference management system as the preferred conference systems for the individuals/groups. A resource account for each of the introduced virtual resources must be created on the Exchange server and made accessible for the Outlook users for scheduling. In this context, a virtual resource is a book able combined resource account of all the conference systems corresponding to one individual or group of individuals.

Figure 2:
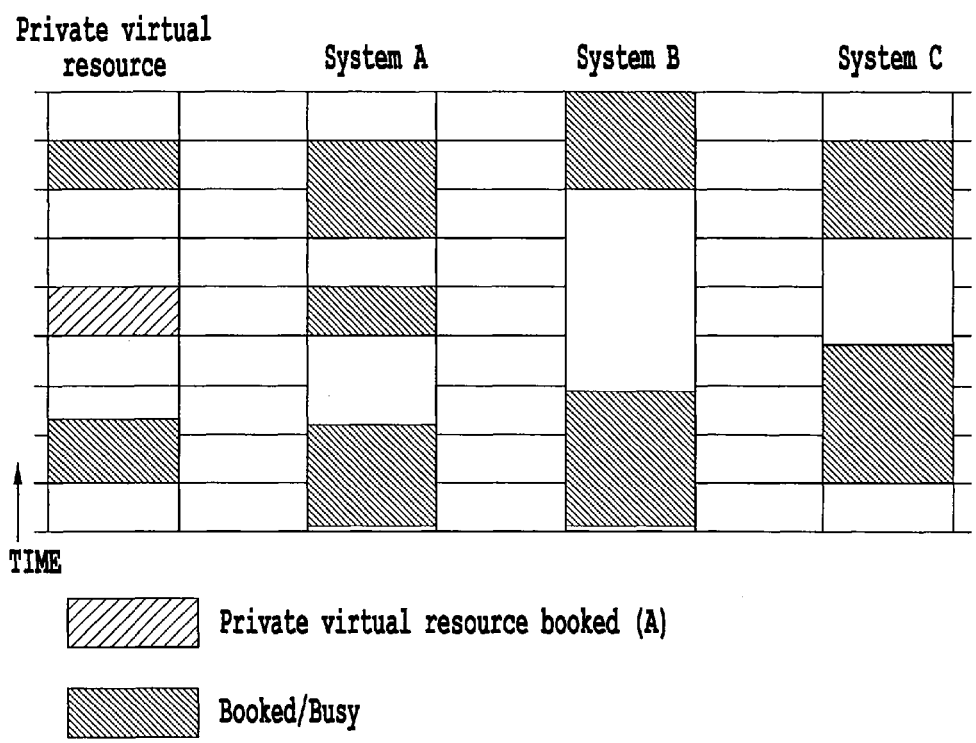
FIG. 2 is a diagram illustrating the relationship between the virtual resource account and associated conference systems according to the present invention.

The relation between the schedule of each conference system and the schedule of the corresponding virtual resource is shown in FIG. 2. Note that in contrast to the diagram of FIG. 1, the time axis is here vertically directed. A virtual resource account will appear as busy at times when all of the physical resources it reflects are booked in the conference management system. At times when the virtual resource is not booked, the virtual resource will appear as free only when at least one of the associated systems are free. As shown in FIG. 2, the virtual resource is marked busy in the periods when all the systems (e.g. video conference endpoints) are busy, and at times when the virtual resource actively has been booked. Even if the schedule of all the conference systems associated with the virtual resource is shown in FIG. 2, only one entry of the virtual resource account will occur in the scheduling session in Outlook, e.g. as an extra bar among the other bars shown in FIG. 1. The free/busy status is preferably written by a synchronizer process running on the Exchange server, which is retrieving booking data from the conference management system.

Figure 3:
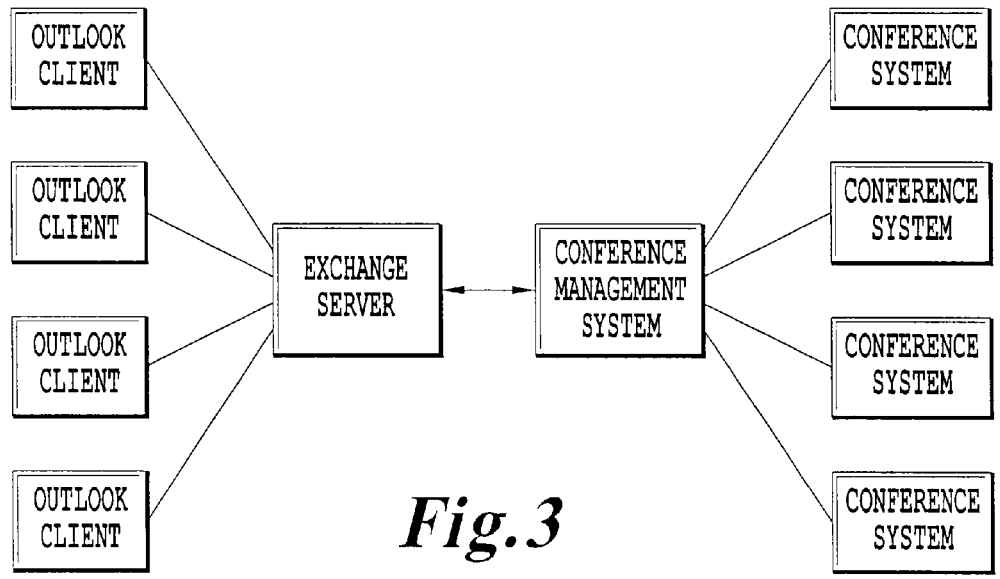
FIG. 3 illustrates the basic architecture of one embodiment of the present invention.
Figure 4:
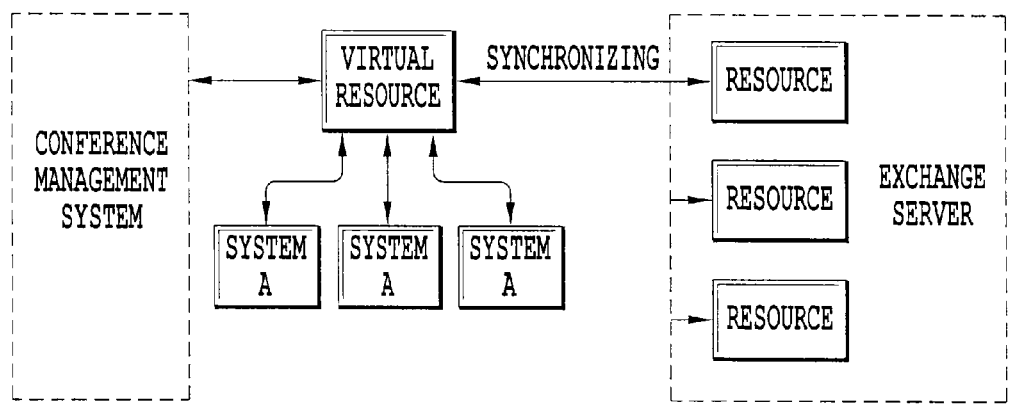
FIG. 4 illustrates a virtual architecture of the synchronization process between a conference management system and an Exchange server according to one embodiment of the present invention.

According to the present invention, all calendar entry operations performed on the virtual resource accounts must first be verified and booked in the management system to which they are connected. Similarly, all other scheduling operations performed in the management system on the virtual resource or on one of the associated conference systems are synchronized into Outlook/Exchange server. The basic architecture for allowing this is shown in FIG. 3.

When requesting a virtual resource to be booked, Outlook will write a calendar entry to its calendar. Before Outlook reports this as succeeded to the user, the Exchange server sends the booking request to the management system for verification/booking. If this is a shared virtual resource (associated with a group of people), this calendar entry will subsequently be removed in whole or partly by the conference management system if any of the other physical resources bound to this virtual resource are available at that time, to allow new bookings at that time. If this is a private virtual resource, this calendar entry will remain in the virtual resource's calendar to reflect that its user is already booked at that time.

The free/busy data the user sees in the Microsoft Outlook client will be generated from the calendar entries in these resource calendars to show when the virtual resource is available for booking. When virtual resource account is associated with a user, the entry of the virtual resource account will appear as busy when the virtual resource actively has been booked or when all the systems associated with the virtual resource are busy. Opposite, the entry of the virtual resource account will appear as free when the virtual resource is not booked and at least one of the systems associated with the virtual resource is free.

The virtual resource could also be associated with a localisation, e.g. the R&D department floor in a big company. Then the rules would be slightly different. The entry of the virtual resource account will appear as busy only when all the systems associated with the virtual resource are busy. Opposite, the entry of the virtual resource account will appear as free when at least one of the systems associated with the virtual resource is free.

From a user's point of view, the present invention, as implemented with Microsoft Outlook and Exchange, will appear by example as follows:

User A would like to schedule a videoconference with the remotely localised User B. User A has no information about the currently preferred video systems of user B, but has a virtual resource associated with User B available in his Outlook calendar. User A selects a time interval for the scheduled conference and invites User B. A booking request is then sent from the Exchange server to the conference management system. In the conference management system, it is investigated whether one of the registered preferred videoconference endpoints of User B is free in the requested time interval. It turns out that system A is free, and this system is then booked in a conventional way by the management system. This may also include automatic configuration and routing between system A and the video conference endpoint of User A. A confirm massage is then returned to the exchange server including information about the selected system. The exchange server updates the status of the virtual resource of User A and User B in the time interval of the scheduled conference, in addition to all virtual resources having system A as one of the preferred video endpoints.

The virtual resources of users not involved in the conference could also be affected. As an example, a User C may have registered system A and B as the preferred video endpoints. System B is already busy in the time interval. However, the virtual resource of User A is still free because System A is not yet booked. When User A schedules the conference with User B, resulting in a booking of System A, then both the preferred video systems of User C is booked in the time interval, and the virtual resource of User C changes from free to busy, even if User C is not involved in the scheduled conference between User A and User B.

Finally, a calendar entry is sent to the User A and B confirming the scheduled conference including information of booked video systems. User B may manually accept or reject the conference, and in case of rejection, the foregoing booking procedure will be reversed and the resources released.

In an alternative embodiment, the virtual resource account and the personal account (as shown in FIG. 1) is combined in Outlook in one single entry. Different status may then be displayed with different colours, having one certain colour for busy in conference provided by the virtual resource account.

As earlier mentioned, the present invention is not limited to Microsoft Outlook, but could be used in any other centrally managed calendar application. In case of using Lotus Notes, the Domino resource database template is modified by adding server agents that verifies and books all resource reservations in the conference management system. A virtual resource can then correspond to a Domino resource in the same way as it is represented as a resource account in the Exchange environment. Before the resources accept the reservations from a Lotus Notes user, an agent on the Domino server requests the conference management system to book and verify the call.

A synchronizer process running on the Domino server refreshes the bookings of these resources by creating reservation documents based on data from the conference management system.

The present invention simplifies call scheduling for the user through well-known calendar user interfaces. Knowledge regarding the type of videoconference systems the remote users prefer to use is not necessary, and it can easily be seen when there is a free video conference system for the remote party/parties. The conference management system finds the video conference systems that together with any required network resources allows the call to be set up.

The invention claimed is:

1. A system comprising:
a memory that stores a list of one or more preferred conference systems for each registered individual or registered group of individuals;
a conference management system that tracks reservation status of the preferred conference systems;
a resource planning application server that creates and maintains a virtual resource account for each registered individual or registered group of individuals, wherein
the virtual resource account represents the one or more preferred conference systems as one bookable entity associated with the registered individual or registered group of individuals, and
the virtual resource account reflects time dependent availability of conference participation by the registered individual or registered group of individuals according to the reservation status of the conference systems represented by the virtual resource account; and
a resource planning application, including a user interface, that displays the virtual resource account and allows a conference to be scheduled with the registered individual or registered group of individuals, associated with the virtual resource account, for a time interval by accepting a reservation of the virtual resource account for the time interval,
wherein the resource planning application, in response to the reservation of the virtual resource account, reserves, for the time interval, an available one of the one or more preferred conference systems represented by the virtual resource account that is subject to the reservation,
said virtual resource account is assigned a status of busy or unavailable when all of the one or more preferred conference systems represented by the virtual resource account are busy or unavailable,
said virtual resource account is assigned a status of free or available when at least one of the one or more preferred conference systems represented by the virtual resource account is free or available, and
the one or more preferred conference systems associated with each individual or group of individuals are arranged in a prioritized order, and when more than one of the preferred conference systems are free or available for the time interval, a conference system of highest priority of the free or available preferred conference systems is reserved.

2. The system according to claim 1, wherein the preferred conference systems are video conference endpoints.

3. The system according to claim 1, wherein the resource planning application server is a Microsoft Exchange server, the resource planning application is Microsoft Outlook, and said user interface is an Attendee Availability in Microsoft Outlook.

4. The system according to claim 1, wherein the resource planning application server is a Domino server, and the resource planning application is Lotus Notes.

5. A method comprising:
obtaining, from a memory, a list of one or more preferred conference systems for each registered individual or registered group of individuals;
tracking, with a conference management system, reservation status of the preferred conference systems;
creating and maintaining, with a resource planning application serve, a virtual resource account for each registered individual or registered group of individuals, wherein
the virtual resource account represents the one or more preferred conference systems as one bookable entity associated with the registered individual or registered group of individuals, and
the virtual resource account reflects time dependent availability of conference participation by the registered individual or registered group of individuals according to the reservation status of the conference systems represented by the virtual resource account;
causing, with a resource planning application, a user interface to be displayed, the user interface displaying the virtual resource account and allowing a conference to be scheduled with the registered individual or registered group of individuals, associated with the virtual resource account, for a time interval by accepting a reservation of the virtual resource account for the time interval;
in response to the reservation of the virtual resource account, reserving, with the resource planning application, for the time interval, an available one of the one or more preferred conference systems represented by the virtual resource account that is subject to the reservation;
assigning said virtual resource account a status of busy or unavailable when all of the one or more preferred conference systems represented by the virtual resource account are busy or unavailable; and
assigning said virtual resource account a status of free or available when at least one of the one or more preferred conference systems represented by the virtual resource account is free or available, wherein
the one or more preferred conference systems associated with each individual or group of individuals are arranged in a prioritized order, and when more than one of the preferred conference systems are free or available for the time interval, the reserving includes reserving a conference system of highest priority of the free or available preferred conference systems.

6. The method according to claim 5, wherein the preferred conference systems are video conference endpoints.

7. The method according to claim 5, wherein the resource planning application server is a Microsoft Exchange server, the resource planning application is Microsoft Outlook, and said user interface is an Attendee Availability in Microsoft Outlook.

8. The method according to claim 5, wherein the resource planning application server is a Domino server, and the resource planning application is Lotus Notes.

* * * * *